US00PP37357P2

(12) United States Plant Patent
Hansen

(10) Patent No.: US PP37,357 P2
(45) Date of Patent: Apr. 7, 2026

(54) ***DELOSPERMA* PLANT NAMED 'Macarena'**

(50) Latin Name: ***Delosperma* hybrid**
Varietal Denomination: Macarena

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,859

(22) Filed: Oct. 14, 2025

(51) Int. Cl.
*A01H 5/02* (2018.01)
*A01H 6/00* (2018.01)

(52) U.S. Cl.
USPC ..... Plt./422

(58) Field of Classification Search
USPC ..... Plt./263.1, 422
See application file for complete search history.

(56) References Cited

U.S. PATENT DOCUMENTS

PP36,547 P2 * 3/2025 Hansen ..... Plt./422

* cited by examiner

*Primary Examiner* — Karen M Redden

(57) ABSTRACT

A new and distinct cultivar of *Delosperma* plant named 'Macarena' is disclosed, characterized by abundant large flowers with petals of bright reddish-orange, a lavender eye and cream-colored anthers in the centers. Plants have a low, mounding habit, and are tolerant to at least USDA zone 6 as well as high heat and drought conditions. The new plant is useful for its bright flowers and low habit in the landscape garden or as a container plant.

1 Drawing Sheet

Latin name of the genus and species: *Delosperma* hybrid.
Variety denomination: 'Macarena'.

STATEMENT REGARDING PRIOR DISCLOSURES UNDER 37 CFR 1.77(B)(6)

The claimed plant was first sold or offered for sale by Walters Gardens, Inc. to North Coast Perennials and North Branch Nursery. on Oct. 15, 2024, by Walters Gardens, Inc., who obtained the plant and all information relating thereto, from the inventor. Subsequently, on Feb. 1, 2025, the new plant was featured in a brief description and photograph on a website operated by Walters Gardens, Inc. and in the "Walters Gardens 2025-2026 Catalog" released on Jun. 3, 2025. Walters Gardens, Inc. obtained the new plant and all information about the new plant from the inventor. No plants of *Delosperma* 'Macarena' have been sold in this country or anywhere in the world nor has any disclosure of the new plant been made more than one year prior to the filing date of this application, and such offer, sale, or disclosure within one year was either derived directly or indirectly from the inventor.

BACKGROUND OF THE INVENTION

The present invention relates to the new and distinct *Delosperma* cultivar named 'Macarena' also referred to here as the new plant. 'Macarena' was hybridized by the inventor at a wholesale perennial nursery in Zeeland, Michigan, USA as the result of a greenhouse cross between 'PJS01S' (not patented) as the female parent and 'PWWG02S' (not patented) in the summer of 2019. Seeds from this pollination were collected in the fall of 2019 and were sown earlier the next year. The new plant originated from a single seedling, was initially evaluated in the summer of 2021, selected for further evaluation, and assigned the breeder code 19-11-3.

*Delosperma* 'Macarena' has been successfully asexually propagated by shoot tip cuttings since 2021 at a wholesale perennial nursery in Zeeland, Michigan and found to produce identical stable and identical plants in successive generations of asexual propagation.

SUMMARY OF THE INVENTION

*Delosperma* 'Macarena' differs from the parents as well as all other Hardy Ice Plant cultivars known to the inventor. The most similar known *Delosperma* cultivars include: 'Dancing Embers' U.S. Plant Pat. No. 36,547, 'PWWG02S' (not patented), 'PJS02S' (not patented), and 'P001S' (not patented).

'Dancing Embers' has flowers having petals of darker reddish-orange with reddish-purple eye and cream centers. 'PJS02S' has more orangish flower petals and the plant is not as winter hardy. 'P001S' has flower petals that are more orange distally with large fuchsia centers.

The female parent, 'PJS01S', has flower petals that are more orange distally with large fuchsia centers. The male parent, 'PWWG02S', has lighter reddish-orange petals and the purplish-pink base in much broader.

*Delosperma* 'Macarena' differs from the above cultivars and all other cultivars of Hardy Ice Plant known to the inventor with the following repeating distinguishing characteristics in combination:

1. Large flowers of bright reddish-orange flowers with lavender eye and cream-colored anthers in the center;
2. Low, mounded habit with good flower coverage, flowering on shoot tips and nodes;

3. Moderately evergreen, winter hardy to at least USDA Zone 6, and with good drought and heat tolerance;

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, and direction may cause the appearance of minor variations in color.

DETAILED BOTANICAL DESCRIPTION

Figure 1:
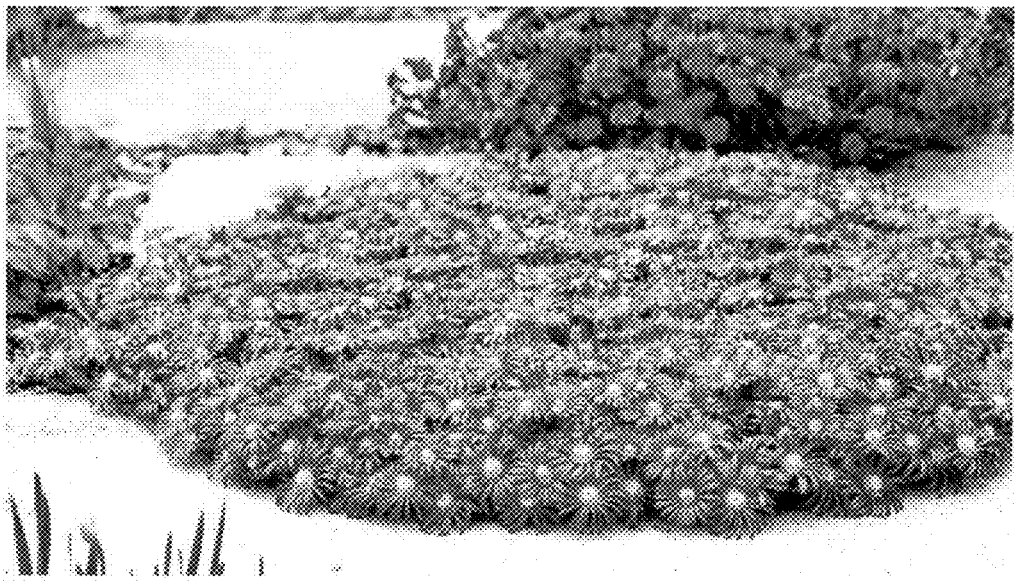
FIG. 1 shows the top-view habit of a three-year-old plant in the landscape.
Figure 2:
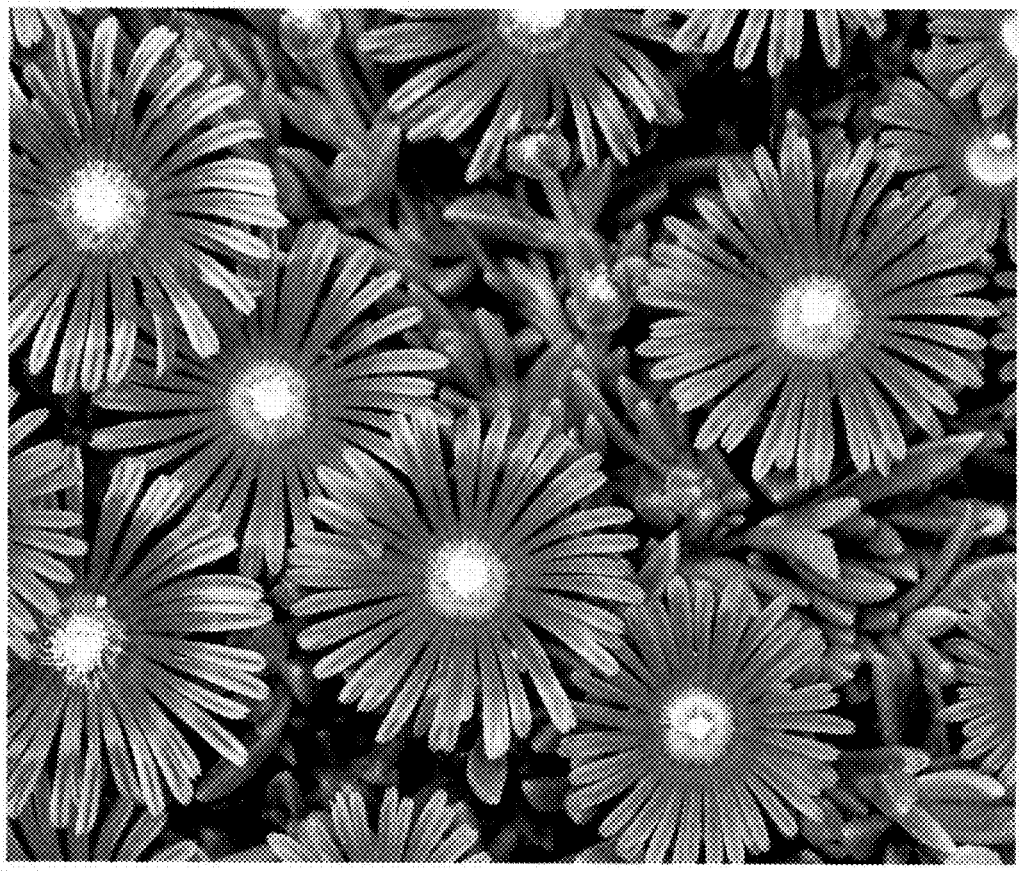
FIG. 2 shows a close-up of the flowers and young buds of a two-year-old plant.

The following is a detailed description of two-year-old plants of the new cultivar grown outdoors in a full sun trial garden with supplemental water and fertilizer as needed at a wholesale nursery in Zeeland, Michigan. No plant growth regulators have been used. Plants of the new cultivar have not been tested under all possible conditions. The phenotype may vary with changes in the environment, climate, and cultural conditions without a change in the genotype. The color reference is in accordance with the 2015 edition of The Royal Horticultural Society Colour Chart except where general color dictionary terms are used.

Botanical designation: *Delosperma* hybrid;

Cultivar denomination: 'Macarena';

Parentage: The female or seed parent is 'PJS01S'; the male or pollen parent is 'PWWG02S';

Asexual propagation: Terminal vegetative cuttings;

Root description: Thin, fibrous, freely branching; color near white depending on soil matrix;

Habit: Low sprawling mound; freely-branching; winter-hardy perennial; to about 86 cm wide and 9 cm tall;

Foliage: Opposite; linear; succulent; with acute apex; truncate partially clasping base; entire margins; slightly concavo-convex; adaxial and abaxial surface glandular and slightly lustrous; to about 29 mm long, 6 mm wide slightly distal to center and 4 mm thick;

Leaf color: Adaxial and abaxial young and mature color between RHS 146D and RHS 145A in basal 3 to 4 mm, adaxial distally nearest RHS NN137A, abaxial distally nearest RHS NN137B; Venation: veins not distinguishable from leaf;

Stem: Stolon; cylindrical; succulent; slightly lustrous; glabrous; glandular distally; to about 22 cm long and 3 mm diameter; branching at nodes;

Nodes: Average about 3 mm thick; average distance about 12 mm apart, greater distances distally and shorter near stem base; node color same as surrounding stem;

Branches: To about 17 cm long and 2 mm diameter;

Docket No. DELMC-25.37 Page 4 of 9

Stem and branch color: Ventrally or low light between RHS 146D and RHS 145B, dorsally in higher light nearest RHS 182D with an undertone of nearest RHS 146D, proximally nearest RHS 161A;

Petiole: Sessile;

Inflorescence: Single; radial; complete; perfect; actinomorphic; one to three flowers per node;

Flower bud: Cylindrical; upright; to about 18 mm tall, 14 mm diameter at apex, and 10 mm diameter at calyx; petal color nearest RHS 46A; sepals nearest RHS 137C distally and at base of hypanthium between RHS 146D and RHS 145A;

Bloom period: Excellent flower coverage beginning late May and continuing for about six weeks and then sporadically through the hottest part of the summer until hard frost in Zeeland, Michigan;

Inflorescence lasting: Two to three days in fully open state; aspect upwardly;

Individual flower size: To about 50 mm across, 16 mm deep;

Petals: To about 36 per flower; linear; apex emarginate with one to two notches about 0.5 mm deep; base truncate; margin entire; highly lustrous metallic sheen adaxial and abaxial; slightly arcuate downwardly; to about 26 mm long and 3 mm across toward apex;

Petal color: When first open adaxial proximal one-quarter nearest RHS N74C, distal three-quarters center nearest RHS 70A, and the distal three-quarters margin between RHS N34A and RHS N34B; when first open abaxial base nearest RHS 72D, distal margin nearest RHS N34B, and in the center nearest RHS 46A; when mature adaxial base nearest 77B, distal margin portion nearest RHS 44A, and distal center nearest RHS 46A; mature abaxial proximal one-third nearest RHS 77B, distal center between RHS 77A and RHS 77B, and distal margin nearest RHS 42A;

Petaloid: About 40 to 55; linear; narrowly acute apex; truncate base; entire margin; to about 7 mm long and 0.5 mm across, decreasing toward center;

Petaloid color: Young adaxial and abaxial proximal portion nearest RHS 76D, and distal portion nearest RHS 6D; maturing to between RHS 72D and RHS N155B;

Sepal: Five, in a single whorl; deltoid; succulent; with acute apex and truncate base; margin entire; adaxial and abaxial glabrous and slightly asperous; size variable, from 7 to 10 mm long above hypanthium and 5 to 6 mm wide at base; with three alternating sepals having dried, hyaline, transparent margins about 2 mm wide extending beyond the edge;

Sepal color: Adaxial color nearest RHS 137B, abaxial nearest RHS;

Pedicel: Cylindrical; glandular; succulent; to about 34 mm long and 3 mm diameter;

Pedicel color: Between RHS 146D and RHS 145B;

Gynoecium: Pentamerous; to about 11 mm long;

Pistil: Five; highly reduced, stigma and style indistinguishable; with stigmatic papillae; conic; to about 3 mm long and 2 mm across; color between RHS 160A and RHS 11A;

Androecium: Quantity about 60 to 80;

*Filament.*—60 to 80; cylindrical; filamentous; mostly straight; glabrous in exterior position filaments, puberulent in distal 1 mm on interior filaments; lustrous; to 4 mm long and 0.3 mm diameter; color variable, base between RHS 75D and RHS 75C, distally nearest RHS NN155D.

*Anther.*—Elliptical; to about 1 mm long and 0.5 mm across; color nearest RHS NN155B.

*Pollen.*—Abundant; color nearest RHS 11D.

Fruit: Penta-dehiscent capsule; to about 13 mm across and 8 mm tall; color at maturity nearest RHS 161C;

Seeds: To about 55 per flower; globose to ellipsoidal; glabrous; about 0.7 mm long and 0.5 mm across; color between RHS 164C and RHS 164D;

Disease resistance: The new plant has not been observed to demonstrate either resistance or susceptibility to diseases and pests that might commonly be found on *Delosperma*.

Growth: The new plant has been shown to be winter hardy to at least USDA Zones 6 and tolerant of drought and high heat conditions.

I claim:

1. A new and distinct cultivar of *Delosperma* plant named 'Macarena' as herein illustrated and described.

* * * * *